(12) United States Patent
Sykes

(10) Patent No.: US 7,332,157 B2
(45) Date of Patent: *Feb. 19, 2008

(54) METHODS FOR HUMAN ALLOGRAFTING

(75) Inventor: Megan Sykes, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 141 days.

This patent is subject to a terminal disclaimer.

(21) Appl. No.: 10/066,294

(22) Filed: Jan. 31, 2002

(65) Prior Publication Data

US 2002/0159999 A1 Oct. 31, 2002

Related U.S. Application Data

(63) Continuation of application No. 09/498,598, filed on Feb. 4, 2000, now abandoned.

(60) Provisional application No. 60/118,894, filed on Feb. 4, 1999.

(51) Int. Cl.
*A01N 63/00* (2006.01)
*A01N 25/00* (2006.01)
*A61K 39/395* (2006.01)
*A61K 35/12* (2006.01)

(52) U.S. Cl. .................. 424/93.7; 424/143.1; 424/572; 514/885

(58) Field of Classification Search .............. 424/93.7, 424/143.1, 572; 514/885
See application file for complete search history.

(56) References Cited

U.S. PATENT DOCUMENTS

| | | | | |
|---|---|---|---|---|
| 5,474,771 | A | 12/1995 | Lederman et al. | 424/133.1 |
| 5,514,364 | A * | 5/1996 | Ildstad | |
| 5,635,156 | A | 6/1997 | Ildstad | 424/1.49 |
| 5,806,529 | A * | 9/1998 | Reisner et al. | |
| 5,817,311 | A | 10/1998 | Bazin et al. | 424/154.1 |
| 5,876,692 | A | 3/1999 | Ildstad | 424/1.49 |
| 5,876,708 | A * | 3/1999 | Sachs | |
| 6,006,752 | A * | 12/1999 | Sykes | |
| 6,558,662 | B2 * | 5/2003 | Sykes et al. | 424/93.1 |

FOREIGN PATENT DOCUMENTS

| | | |
|---|---|---|
| WO | WO 93/06852 | 4/1993 |
| WO | WO95/11692 | 5/1995 |
| WO | WO 95/11692 | 5/1995 |
| WO | WO 95/24217 | 9/1995 |
| WO | WO 97/41863 | 11/1997 |
| WO | WO 99/03502 | 1/1999 |
| WO | WO99/03502 | 1/1999 |
| WO | WO 99/25367 | 5/1999 |

OTHER PUBLICATIONS

Benkerrou et al., Blood, 1998, vol. 92, pp. 3137-3147.*

Manilay et al., "Intrathymic Deletion of Alloreactive T Cells in Mixed Bone Marrow Chimeras Prepared With a Nonmyeloablative Conditioning Regimen", Transplantation, vol. 66, No. 1, pp. 96-102, 1998.
Schad et al., "Anti-CD2 Monoclonal antibody Elicits Specific Alloantigen Hyporesponsiveness", Faseb Journal, vol. 10, No. 6, p. A1313, 1996.
Sykes et al., "Xenograft Tolerance", Immunological Reviews, No. 141, pp. 245-276, 1994.
Wekerle et al., "Extrathymic T Cell Deletion and Allogeneic Stem Cell Engraftment Induced With Costimulatory Blockade Is Followed by Central T Cell Tolerance", Journal of Experimental Medicine, vol. 187, No. 12, pp. 2037-2044, 1998.
Wekerle et al., "Anti-CD154 or CTLA4lg Obviates the Need for Thymic Irradiation in a Non-Myeloablative Conditioning Regimen for the Induction of Mixed Hematopooietic Chimerism and Tolerance", Transplantation, vol. 68, No. 9, pp. 1348-1355, 1999.
Woodward et al., "Blockade of Multiple Costimulatory Receptors Induces Hyporesponsiveness", Transplantation, vol. 62, No. 7, pp. 1011-1018, 1996.
Colson, Y.L. et al. (1995) "A Nonlethal Conditioning Approach to Achieve Durable Multilineage Mixed Chimerism and Tolerance Across Major, Minor, and Hematopoietic Histocompatibility Barriers". *J. Immunology* 153:4179-4188.
Kawai, T. et al. (1995) "Mixed Allogeneic Chimerism and Renal Allograft Tolerance in Cynomolgus Monkeys". *Transplantation* 59(2): 256-262.
Kimikawa, M. et al. (1997) "Modifications of the Conditioning Regimen for Achieving Mixed Chimerism and Donor-Specific Tolerance in Cynomolgus Monkeys". *Transplantation* 64(5): 709-716.
Kimikawa, M. et al. (1997) "Mixed Chimerism and Transplantation Tolerance Induced by a Nonlethal Preparative Regimen in Cynomolgus Monkeys". *Trans Proc 29*:1218.
Kirk, A.D. et al. (1997) "CTLA4-Ig and anti-CD40 ligand prevent renal allograft rejection in primates". *Proc. Natl. Acad. Sci 94*: 8789-8794.
Li, H. et al. (1995) "Mixed Allogeneic Chimerism Achieved by Lethal and Nonlethal Conditioning Approaches Induces Donor-Specific Tolerance to Simultaneous Islet Allografts". *Transplantation 60*(6): 523-529.
Monaco, A.P. et al. (1976) "Possible active enhancement of human cadaver renal allograft with antilymphocyte serum (ALS) and donor bone marrow: Case report of an initial attempt". *Surgery 79*(4): 384-392.
Sharabi, Y. et al. (1989) "Mixed Chimerism and Permanent Specific Transplantation Tolerance Induced by a Nonlethal Preparative Regimen". *J. Exp. Med. 169*: 493-502.
Sharabi, Y. et al. (1989) "Engraftment of Allogeneic Bone Marrow Following Administration of Anti-T Cell Monoclonal Antibodies and Low-Dose Irradiation". *Trans. Proc. 21*(1): 233-235.

(Continued)

*Primary Examiner*—Michail Belyavskyi
(74) *Attorney, Agent, or Firm*—Fish & Richardson P.C.

(57) ABSTRACT

A method of preparing a human recipient for a graft from a human which includes: inducing mixed chimerism in the recipient (e.g., by administering to the recipient irradiation or chemotherapy), administering thymic irradiation, administering an antibody that depletes T cells, administering donor hematopoietic progenitor cells to the recipient, and administering an immunosuppressant.

20 Claims, No Drawings

OTHER PUBLICATIONS

Storb, R. et al. (1997) "Stable Mixed Hematopoietic Chimerism in DLA-Identical Littermate Dogs Given Sublethal Totaly Body Irradiation Before and Pharmacological Immunosuppression After Marrow Transplantation". *Blood* 89(8): 3048-3054.

Sykes, M. et al. (1997) "Induction of high levels of allogeneic hematopoietic reconstitution and donor-specific tolerance without myelosuppressive conditioning". *Nature Medicine* 3: 783-787.

Xia et al. (1990) "Rat Monoclonal Antibodies Specific for Human T. Lymphocytes". *In Rat Hybridomas and Rat Monoclonal Antibodies*, Ed. H. Bazin, CRC Press, Inc., Boca Raton, Florida, 309-322.

Emerson, S.G. (1996) "Ex Vivo Expansion of Hematopoietic Precursors, Progenitors, and Stem Cells: The Next Generation of Cellular Therapies". *Blood* 87: 3082-3088.

Petzer, A.L. et al. (1996) "Self-renewal of primitive hematopoietic cells (long-term-culture-intiating cells) in vitro and their expansion in a defined medium". *Proc. Natl. Acad. Sci. USA* 93: 1470-1474.

Zandstra, P.W. et al. (1994) "Expansion of Hematopoietic Progenitor Cell Populations in Stirred Suspension Bioreactors of Normal Human Bone Marrow Cells". *Bio/Technology* 12: 909-914.

Colson et al., "A Nonlethal Conditioning Approach to Achieve Durable Multilineage Mixed Chimerism and Tolerance Across Major, Minor, and Hematopoietic Histocompatibility Barriers" *J. Immunology* 153:4179-4188 (1995).

Emerson, "Ex Vivo Expansion of Hematopoietic Precursors, Progenitors, and Stem Cells: The Next Generation of Cellular Therapies" *Blood* 87:3082-3088 (1996).

Kawai et al., "Mixed Allogeneic Chimerism and Renal Allograft Tolerance in Cynomolgus Monkeys" *Transplantation* 59(2):256-262 (1995).

Kimikawa et al., "Mixed Chimerism and Transplantation Tolerance Induced by a Nonlethal Preparative Regimen in Cynomolgus Monkeys" *Trans. Proc.* 29:1218 (1997).

Kimikawa et al., "Modifications of the Conditioning Regimen for Achieving Mixed Chimerisms and Donor-Specific Tolerance in Cynomolgus Monkeys" *Transplantation* 64(5):709-716 (1997).

Kirk et al., "CTLA4-lg and anti-CD40 ligand prevent renal allograft rejection in primates" *PNAS USA* 94:8789-8794 (1997).

Li et al., "Mixed Allogeneic Chimerism Achieved by Lethal and Nonlethal Conditioning Approaches Induces Donor-Specific Tolerance to Simultaneous Islet Allografts" *Transplantation* 60(6):523-529 (1995).

Manilay et al., "Intrathymic Deletion of Alloreactive T Cells in Mixed Bone Marrow Chimeras Prepared with a Nonmyeloablative Conditioning Regimen" *Transplantation* 66(1):96-102 (1998).

Monaco et al., "Possible active enhancement of human cadaver renal allograft with antilymphocyte serum (ALS) and donor bone marrow: Case report of an initial attempt" *Surgery* 79(4):384-392 (1976).

Petzer et al., "Self-renewal of primitive hematopoietic cells (long-term-culture-initiating cells) in vitro and their expansion in defined medium" *PNAS USA* 93:1470-1474 (1996).

Schad et al., "Anti-CD2 Monoclonal antibody Elicits Specific Alloantigen Hyporesponsiveness" *Faseb. J.* 10(6):A1313 (1996).

Sharabi et al., "Engraftment of Allogeneic Bone Marrow Following Administration of Anti-T Cell Monoclonal Antibodies and Low-Dose Irradiation" *Trans. Proc.* 21(1):233-235 (19890.

Sharabi et al., "Mixed Chimerism and Permanent Specific Transplantation Tolerance Induced by a Nonlethal Preparative Regimen" *J. Exp. Med.* 169:493-502 (1989).

Storb et al., "Stable Mixed Hematopoietic Chimerism in DLA-Identical Littermate Dogs Given Sublethal Total Body Irradiation Before and Pharmacological Immunosuppression After Marrow Transplantation" *Blood* 89(8):3048-3054 (1997).

Sykes et al., "Induction of high levels of allogeneic hematopoietic reconstitution and donor-specific tolerance without myelosuppressive conditioning" *Nature Medicine* 3:783-787 (1997).

Sykes et al., "Xenograft Tolerance" *Immunological* 141:245-276 (1994).

Wekerle et al., "Anti-CD154 or CTLA4lg Obviates the Need for Thymic Irradiation in a Non-Myleoablative Conditioning Regimen for the Induction of Mixed Hematopoietic Chimerism and Tolerance" *Transplantation* 68(9):1348-1355 (1999).

Wekerle et al., "Extrathymic T Cell Deletion and Allogeneic Stem Cell Engraftment Induced with Costimulatory Blockade is Followed by Central T Cell Tolerance" *J. Experimental Med.* 187(12):2037-2044 (1998).

Woodward et al., "Blockade of Multiple Costimulatory Receptors Induces Hyporesponsiveness" *Transplantation* 62(7):1011-1018 (1996).

Xia et al., "Rat Monoclonal Antibodies Specific for Human T. Lymphocytes" *In Rat Hybridomas and Rat Monoclonal Antibodies* Ed.H. Bazin, CRC Press, Inc., Boca Raton, FL 309-322 (1990).

Zandstra et al., "Expansion of Hematopoietic Progenitor Cell Population in Stirred Suspension Bioreactors of Normal Human Bone Marrow Cells" *Bio/Technology* 12:909-914 (1994).

* cited by examiner

METHODS FOR HUMAN ALLOGRAFTING

RELATED APPLICATIONS

This application is a continuation of U.S. Ser. No. 09/498,598, filed on Feb. 4, 2000, now abandoned which claims priority to U.S. Provisional Application No. 60/118,894, filed on Feb. 4, 1999, the contents of which are hereby incorporated by reference.

BACKGROUND OF THE INVENTION

The invention relates to tissue and organ transplantation.

SUMMARY OF THE INVENTION

In another aspect, the invention features a method of preparing a recipient, e.g., a human patient, for a graft from a donor mammal of the same species. The method includes:

Creating hematopoietic space in the recipient, e.g., by administering to the recipient an amount of irradiation or chemotherapy sufficient to allow the induction of mixed chimerism in the recipient. The irradiation should be administered in two (or more) separate doses, preferably equal doses. By way of example, 300 cGy of whole body irradiation can be administered as 150 cGy on each of two successive days of whole body irradiation. The irradiation step can be replaced by chemotherapy described below;

Administering to the recipient one or more chemotherapeutic agents, e.g., cyclophosphamide, busulfan, fludararabine, or any combination thereof. The chemotherapeutic agent can be a radiomimetic (i.e. an agent that interacts with DNA in a mechanism similar to ionizing radiation) or a non-radiomimetic. In one embodiment, a single-agent chemotherapeutic regimen is administered. For example, cyclophosphamide can be administered (preferably, intravenously) at a dose of 50 mg/kg/day for three consecutive days (e.g., on days −5, −4 and −3 prior to administration of stem cells or bone marrow on day 0). Alternatively, a combination of agents, e.g., cyclophosphamide, busulfan and/or fludararabine, can be used. Exemplary combinations include cyclophosphamide and fludararabine, and cyclophosphamide and busulfan. Analogues of these compounds may also be incorporated into the final regimen, e.g., substituting treosulfan for busulfan; purine or nucleoside analogs of these agents, e.g., fludarabine. The combination of agents can be administered sequentially or, preferably, concurrently. Preferably, the cyclophosphamide is administered intravenously.

Creating thymic space in the recipient, e.g., by administering to the recipient, an amount of thymic irradiation sufficient to kill or otherwise inactivate recipient thymocytes. By way of example, 700 cGy of thymic irradiation can be administered to the recipient. This step can be replaced with other methods of creating thymic space, described below;

Administering to the recipient, one or more doses of at least one antibody which depletes T cells. The antibodies can be administered before, on, or after, the day of graft implantation. In a preferred embodiment the antibodies are administered up to or on the day of graft implantation. Suitable antibodies include, anti-CD4, anti-CD8, and anti-CD2 antibodies. Anti-CD2 antibodies are preferred. For example, the method can include, administering to the recipient, an anti-CD2 monoclonal antibody, e.g., administering to the recipient, at least one dose, and possibly two, three or four, doses of an anti-CD2 monoclonal antibody, e.g., before or up to the day of graft implantation. By way of example, four doses of an anti-CD2 monoclonal antibody, e.g., MEDI-507, can be administered. Optionally, the doses should be more or less evenly spaced. The last can occur the day before transplantation, e.g., doses administered on days −4, −3, −2, −1 (wherein day 0 is the day of graft transplant and day −1 is the day prior to day 0). A dose of 0.1 mg/kg on day −4 and of 1.0 mg/kg on days −3, −2, and −1, of the anti-CD2 monoclonal antibody MEDI-507 has been found to be effective. Alternatively, the antibody may be administering up to several weeks prior to the graft implantation. As one example, a dose of 0.1 mg/kg can be administered on day −7, and a single dose of 0.5 mg/kg can be administering on day −6. Analogous doses of other anti-CD2 antibodies can be used;

Optionally, administering to the recipient, a treatment which reduces the side effects on the administration of anti-T cell antibodies, e.g., administering an agent which suppresses the release of antibody-induced cytokine release. By way of example, the method can include administering to the recipient, a steroid immunosuppressant, e.g., methylprednisolone. The immunosuppressant can be administered prior to one or more, e.g., prior to each, or prior to the first, administration of a T cell depleting antibody, e.g., an anti-CD2 antibody. By way of example, an intravenous dose of methylprednisolone sodium succinate, 8 mg/kg, to a maximum dose of 500 mg has been found to be effective. The methylprednisolone can be administered 1-4 hours (preferably, between 1 and 2 hours) before antibody administration.

Optionally, administering a treatment which inhibits or depletes splenic T cells and/or B cells. Examples of such treatment include the administration of anti-T cell antibodies, anti-B cell antibodies or immunosuppressive agents, in sufficient dosage to inhibit or deplete splenic antibodies, or performing a splenectomy. In a preferred embodiment the method includes performing a splenectomy on the recipient, e.g., on the day of transplantation day 0. Preferably, the recipient is not splenectomized when an anti-CD40 ligand is administered;

Administering to the recipient, donor hematopoietic progenitor cells, e.g., donor hematopoietic bone marrow cells. Mobilized donor peripheral blood progenitor cells are preferred. Bone marrow can also be used as a source of cells. Hematopoietic stem cells can be administered before, after, or on the day of transplantation (day 0); and Administering to the recipient, a non-chronic course of an immunosuppressant, e.g., cyclosporine or FK506. By way of example, an immunosuppressant can be administered from the day of transplant but discontinued after stable chimerism has been established. The dose of an immunosuppressant can be given in two phases, a first phase in which a chosen level of immunosuppressant is established, e.g., a level sufficient to inhibit graft-reactive T cells, followed by a phase in which the dose is tapered. E.g., cyclosporine can be administered to provide a trough whole blood concentration of 400-500 ng/mL, for 35 days, then tapered over 7 days and discontinued on Day 42).

In preferred embodiments, the method includes the step of introducing into the recipient, a graft obtained from the donor. The graft can be other than hematopoietic stem cells or bone marrow, e.g., a heart, pancreas, liver, or kidney.

In a preferred embodiment the donor is related to the recipient, e.g., is a sibling, parent, or cousin.

In a preferred embodiment the donor is not related to the recipient.

In a preferred embodiment the graft is from a cadaver.

In a preferred embodiment the method includes:

administering to a human recipient, 300 cGy (150 cGy on each of two successive days) of whole body irradiation;

administering to the recipient, 700 cGy of thymic irradiation;

administering a T cell depleting antibody, e.g., an anti-CD2 monoclonal antibody, e.g., administering an anti-CD2 monoclonal antibody, e.g., MEDI-507, on days −4, −3, −2, −1;

optionally, administering a steroid immunosuppressant, e.g., prior to the first, or each, antibody administration, e.g., administering a dose of methylprednisolone sodium succinate, prior to the first, or each, antibody administration;

optionally, performing a splenectomy on the recipient, e.g., on the day of transplantation day 0;

administering to the recipient donor peripheral blood progenitor cells, e.g., on the day of transplantation day 0; and administering to the recipient a non-chronic course of an immunosuppressant, e.g., cyclosporine started on the day prior to transplantation. By way of example, starting on the day after transplantation (Day 1), cyclosporine can be administered to provide a trough whole blood concentration of 400-500 ng/mL, for 35 days, then tapered over 7 days and discontinued on Day 42).

In another aspect, the invention features a method of preparing a recipient, e.g., a human patient, for a graft from a donor mammal of the same species, without the administration of whole body irradiation. The method includes:

Creating thymic space in the recipient, e.g., by administering to the recipient, an amount of thymic irradiation sufficient to kill or otherwise inactivate recipient thymocytes. By way of example 1,000 cGy of thymic irradiation can be administered to the recipient. This step can be replaced with other methods of creating thymic space, as is described below; Administering to the recipient, one or more doses of at least one antibody which depletes T cells. The antibodies can be administered before, on, or after, the day of graft implantation. In a preferred embodiment the antibodies are administered up to or on the day of graft implantation. Suitable antibodies include, anti-CD4, anti-CD8, and anti-CD2 antibodies. Anti-CD2 antibodies are preferred. For example, the method can include, administering to the recipient, an anti-CD2 monoclonal antibody, e.g., administering to the recipient, at least two, three or four, doses of an anti-CD2 monoclonal antibody, e.g., before or up to the day of graft implantation. By way of example, four doses of an anti-CD2 monoclonal antibody, e.g., MEDI-507, can be administered. The doses should be more or less evenly spaced with the last occurring the day before transplantation, e.g., doses administered on days −4, −3, −2, −1. A dose of 0.1 mg/kg on day −4 and of 1.0 mg/kg on days −3, −2, and −1, of the anti-CD2 monoclonal antibody MEDI-507 has been found to be effective. Analogous doses of other anti-CD2 antibodies can be used;

Optionally, administering to the recipient, a treatment which reduces the side effects on the administration of anti-T cell antibodies, e.g., administering an agent which suppresses the release of antibody-induced cytokine release. By way of example, the method can include administering to the recipient, a steroid immunosuppressant, e.g., methylprednisolone. The immunosuppressant can be administered prior to one or more, e.g., prior to each, or prior to the first, administration of a T cell depleting antibody, e.g., an anti-CD2 antibody. By way of example, an intravenous dose of methylprednisolone sodium succinate, 8 mg/kg, to a maximum dose of 500 mg has been found to be effective. The methylprednisolone can be administered 1-4 hours (preferably, between 1 and 2 hours) before antibody administration;

Optionally, administering a treatment which inhibits or depletes splenic T cells and/or B cells. Examples of such treatment include the administration of anti-T cell antibodies, anti-B cell antibodies or immunosuppressive agents, in sufficient dosage to inhibit or deplete splenic antibodies, or performing a splenectomy. In a preferred embodiment the method includes performing a splenectomy on the recipient, e.g., on the day of transplantation day 0;

Administering to the recipient, donor hematopoietic progenitor cells, e.g., donor hematopoietic bone marrow cells. Mobilized donor peripheral blood progenitor cells are preferred. Hematopoietic stem cells can be administered before, after, or on the day of transplantation (day 0). An amount of donor hematopoietic stem cells sufficient to result in mixed chimerism in the absence of whole body irradiation is administered; and Administering to the recipient, a non-chronic course of an immunosuppressant, e.g., cyclosporine or FK506. By way of example, an immunosuppressant can be administered from the day of transplant but discontinued after stable chimerism has been established. The dose of an immunosuppressant can be given in two phases, a first phase in which a chosen level of immunosuppressant is established, e.g., a level sufficient to inhibit graft-reactive T cells, followed by a phase in which the dose is tapered. E.g., cyclosporine can be administered to provide a trough whole blood concentration of 400-500 ng/mL, for 35 days, then tapered over 7 days and discontinued on Day 42).

In preferred embodiments, the method includes the step of introducing into the recipient, a graft obtained from the donor. The graft can be other than hematopoietic stem cells or bone marrow, e.g., a heart, pancreas, liver, or kidney.

In a preferred embodiment the donor is related to the recipient, e.g., is a sibling, parent, or cousin.

In a preferred embodiment the donor is not related to the recipient.

In a preferred embodiment the graft is from a cadaver or a living donor.

In a preferred embodiment the method includes:

administering to a human recipient, 1,000 cGy of thymic irradiation;

administering a T cell depleting antibody, e.g., an anti-CD2 monoclonal antibody, e.g., administering an anti-CD2 monoclonal antibody, e.g., MEDI-507, on days −4, −3, −2, −1;

optionally, administering a steroid immunosuppressant, e.g., prior to the first, or each, antibody administration, e.g., administering a dose of methylprednisolone sodium succinate, prior to the first, or each, antibody administration;

optionally, performing a splenectomy on the recipient, e.g., on the day of transplantation day 0;

administering to the recipient donor peripheral blood progenitor cells, e.g., on the day of transplantation day 0; and administering to the recipient a non-chronic course of an immunosuppressant, e.g., cyclosporine started on the day prior to transplantation. By way of example, starting on the day after transplantation (Day 1), cyclosporine can be administered to provide a trough whole blood concentration of 400-500 ng/mL, for 35 days, then tapered over 7 days and discontinued on Day 42).

In another aspect, the invention features a method of preparing a recipient, e.g., a human patient, for a graft from a donor mammal of the same species, without the administration of whole body irradiation, and thymic irradiation. The method includes:

Administering to the recipient, one or more doses of an antibody which depletes T cells. The antibodies can be administered before, on or after, the day of graft implantation. In a preferred embodiment the antibodies are administered up to or on the day of graft implantation. Suitable antibodies include, anti-CD4, anti-CD8, and anti-CD2 antibodies. Anti-CD2 antibodies are preferred. For example, the method can include, administering to the recipient, an anti-CD2 monoclonal antibody, e.g., administering to the recipient, at least one dose, and possibly two, three or four, doses of an anti-CD2 monoclonal antibody, e.g., before or up to the day of graft implantation. By way of example, four doses of an anti-CD2 monoclonal antibody, e.g., MEDI-507, can be administered. The doses should be more or less evenly spaced with the last occurring the day before transplantation, e.g., on days −4, −3, −2, −1. A dose of 0.1 mg/kg on day −4 and of 1.0 mg/kg on days −3, −2, and −1, of the anti-CD2 monoclonal antibody MEDI-507 has been found to be effective. Analogous doses of other anti-CD2 antibodies can be used;

Optionally, administering to the recipient, a treatment which reduces the side effects on the administration of anti-T cell antibodies, e.g., administering an agent which suppresses the release of antibody-induced cytokine release. By way of example, the method can include administering to the recipient, a steroid immunosuppressant, e.g., methylprednisolone. The immunosuppressant can be administered prior to one or more, e.g., prior to each, or prior to the first, administration of a T cell depleting antibody, e.g., an anti-CD2 antibody. By way of example, an intravenous dose of methylprednisolone sodium succinate, 8 mg/kg, to a maximum dose of 500 mg has been found to be effective. The methylprednisolone can be administered 1-4 hours (preferably, between 1 and 2 hours) before antibody administration;

Optionally, administering a treatment which inhibits or depletes splenic T cells and/or B cells. Examples of such treatment include the administration of anti-T cell antibodies, anti-B cell antibodies or immunosuppressive agents, in sufficient dosage to inhibit or deplete splenic antibodies, or performing a splenectomy. In a preferred embodiment the method includes, performing a splenectomy on the recipient, e.g., on the day of transplantation day 0;

Administering to the recipient, donor hematopoietic progenitor cells, e.g., donor hematopoietic bone marrow cells. Mobilized donor peripheral blood progenitor cells are preferred. Hematopoietic stem cells can be administered before, after, or on the day of transplantation (day 0). An amount of donor hematopoietic stem cells sufficient to result in mixed chimerism in the absence of whole body irradiation and thymic irradiation is administered;

Optionally, administering to the recipient, a non-chronic course of an immunosuppressant, e.g., cyclosporine or FK506. By way of example, an immunosuppressant can be administered from the day of transplant but discontinued after stable chimerism has been established. The dose of an immunosuppressant can be given in two phases, a first phase in which a chosen level of immunosuppressant is established, e.g., a level sufficient to inhibit graft-reactive T cells, followed by a phase in which the dose is tapered. E.g., cyclosporine can be administered to provide a trough whole blood concentration of 400-500 ng/mL, for 35 days, then tapered over 7 days and discontinued on Day 42); and Administering to the recipient, an inhibitor, e.g., a blocker, of a costimulatory pathway (e.g., a blocker, e.g., an inhibitor, e.g., one or both of a blocker of the CD40 ligand-CD40 interaction and a blocker of the CD28-B7 interaction). A blocker of the CD40/CD40L interaction, e.g., an anti-CD40L antibody can be administered prior to administration of a blocker of the CD28/B7 interaction, e.g., CTLA4/Ig. The CD40/CD40L blocker can be administered on the day donor tissue is introduced and the CD28/B7 blocker administered 2, 3, 4 5 or more days later.

In preferred embodiments the CD40 ligand-CD40 interaction is inhibited by administering an antibody or soluble ligand or receptor for the CD40 ligand or CD40, e.g., by administering an anti-CD40L antibody, e.g., 5c8 (see U.S. Pat. No. 5,474,711, hereby incorporated by reference) or an antibody with similar efficacy or an antibody whose epitope overlaps that of 5c8. Preferably the inhibitor binds the CD40 ligand.

In preferred embodiments the CD28-B7 interaction is inhibited by administering a soluble ligand or receptor or antibody for the CD28 or B7, e.g., a soluble CTLA4, e.g., a CTLA4 fusion protein, e.g., a CTLA4 immunoglobulin fusion, e.g., CTLA4/Ig. Preferably, the inhibitor binds B7. In preferred embodiments anti-B7-1 or anti-B7-2 antibodies are administered.

In preferred embodiments CTLA4-Ig and an anti-CD40L antibody are administered.

In preferred embodiments, the method includes the step of introducing into the recipient, a graft obtained from the donor. The graft can be other than hematopoietic stem cells or bone marrow, e.g., a heart, pancreas, liver, or kidney.

In a preferred embodiment the donor is related to the recipient, e.g., is a sibling, parent, or cousin.

In a preferred embodiment the donor is not related to the recipient.

In a preferred embodiment the graft is from a cadaver.

In a preferred embodiment the method includes:
administering a T cell depleting antibody, e.g., an anti-CD2 monoclonal antibody, e.g., administering an anti-CD2 monoclonal antibody as a single or multiple infusions(s) prior to the graft. In one preferred embodiment, a single infusion (with or without a test dose given the day before) is administered a week prior to the graft. In another preferred embodiment, multiple administrations are given at regularly-spaced intervals, e.g., on days −4, −3, −2, −1;

optionally, administering a steroid immunosuppressant, e.g., prior to the first, or each, antibody administration, e.g., administering a dose of methylprednisolone sodium succinate, prior to the first, or each, antibody administration;

optionally, performing a splenectomy on the recipient, e.g., on the day of transplantation day 0;

administering to the recipient, donor peripheral blood progenitor cells, e.g., on the day of transplantation (day 0), in an amount sufficient to result in mixed chimerism in the absence of whole body irradiation and thymic irradiation;

optionally, administering to the recipient, non-chronic course of an immunosuppressant, e.g., cyclosporine started on the day prior to transplantation. By way of example, starting on the day after transplantation (Day 1), cyclosporine can be administered to provide a trough whole blood concentration of 400-500 ng/mL, for 35 days, then tapered over 7 days and discontinued on Day 42); and administering to the recipient, an inhibitor, e.g., a blocker, of a costimulatory pathway (e.g., a blocker, e.g., an inhibitor, e.g., one or both a blocker of the CD40 ligand-CD40 interaction and a blocker of the CD28-B7 interaction). A blocker of the CD40/CD40L interaction, e.g., an anti-CD40L antibody can be administered prior to administration of a blocker of the CD28/B7 interaction, e.g., a soluble CTLA4, e.g., a CTLA4 fusion protein, e.g., a CTLA4 immunoglobulin fusion, e.g., CTLA4/Ig. The CD40/CD40L blocker can be administered on the day donor tissue is introduced and the CD28/B7 blocker administered 2, 3, 4 5 or more days later.

In preferred embodiments the CD40 ligand-CD40 interaction is inhibited by administering an antibody or soluble ligand for the CD40 ligand or CD40, e.g., by administering an anti-CD40 or CD40L antibody, e.g., MR-1, or an antibody which binds the MR-1 epitope. Preferably the inhibitor binds the CD40 ligand.

In preferred embodiments the CD28-B7 interaction is inhibited by administering a soluble ligand or antibody for the CD28 or B7, e.g., soluble CTLA4, e.g., a soluble CTLA4 fusion protein, e.g., a CTLA4-Ig fusion protein.

In preferred embodiments CTLA4-1 gG or an anti-B7 antibody are administered.

"Hematopoietic space", as used herein, refers to a condition created in the bone marrow which promotes engraftment of administered stem cells. The most common way of creating hematopoietic space is by irradiation of the bone marrow with whole body irradiation. Alternatively, hematopoietic space can be created with the use of radiomimetic chemotherapeutic agents, either alone or in combination with other chemotherapeutic (e.g., antimetabolite and/or antineoplastic) agents. In another embodiment, hematopoietic space can be created with the use of non-radiomimetic chemotherapeutic agents. Such agents might include fludarabine or other purine or deoxynucleoside analogues, such as 2-CDA, 6-MP, 6-TG, gemcitabine or cytarabine.

"Thymic space" as used herein, is a state created by a treatment that facilitates the migration to and/or development in the thymus of donor hematopoietic cells of a type which can delete or inactivate host thymocytes that recognize donor antigens. It is believed that the effect is mediated by elimination of host cells in the thymus.

"Graft", as used herein, refers to a body part, organ, tissue, or cells. Organs such as liver, kidney, heart or lung, or other body parts, such as bone or skeletal matrix, tissue, such as skin, intestines, endocrine glands, or progenitor stem cells of various types, are all examples of grafts.

"Thymic irradiation", as used herein, refers to a treatment in which at least half, and preferably at least 75, 90, or 95% of the administered irradiation is targeted to the thymus. Whole body irradiation, even if the thymus is irradiated in the process of delivering the whole body irradiation, is not considered thymic irradiation.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes.

A non-chronic course of an immunosuppressant refers to the administration of an immunosuppressant, e.g., cyclosporine or FK506. In a preferred embodiment, the immunosuppressant is administered in an amount sufficient such that T cell dependent rejection is inhibited. In a preferred embodiment administration dose not extend beyond 2, 4, 6, 12, or 18 months after graft implantation. By way of example, starting on the day after transplantation (Day 1), the dose of cyclosporine can be 4 mg/kg given twice a day, and adjusted to provide a trough whole blood concentration of 400-500 ng/mL, as measured by a monoclonal antibody based assay (or the equivalent if a different assay or serum rather than whole blood are used) for 35 days, then tapered over 7 days and discontinued on Day 42.

"Tolerance", as used herein, refers to an inhibition of a graft recipient's immune response which would otherwise occur, e.g., in response to the introduction of a nonself MHC antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Tolerance, as used herein, refers to a donor antigen-specific inhibition of the immune system as opposed to the broad spectrum inhibition of the immune system seen with immunosuppressants.

"A blocker" as used herein, refers to a molecule which binds a member of a ligand/counter-ligand pair and inhibits the interaction between the ligand and counter-ligand or which disrupts the ability of the bound member to transduce a signal. The blocker can be an antibody (or fragment thereof) to the ligand or counter ligand, a soluble ligand (soluble fragment of the counter ligand), a soluble counter ligand (soluble fragment of the counter ligand), or other protein, peptide or other molecule which binds specifically to the counter-ligand or ligand, e.g., a protein or peptide selected by virtue of its ability to bind the ligand or counter ligand in an affinity assay, e.g., a phage display system.

The use of the article "a" or "an" is non limiting with regard to number except where clearly indicated to be limited by the context. E.g., methods which include administering "an" antibody or a dose can include administering one or more than one antibodies or doses.

Methods of the invention minimize or eliminate the need for hematopoietic space-creating treatment, e.g., irradiation, in many methods of tolerance induction.

Other features and advantages of the invention will be apparent from the following detailed description, and from the claims.

DETAILED DESCRIPTION

Hematopoietic Stem Cells

Some methods described herein include administering a sufficiently large number of donor hematopoietic cells to the recipient such that, donor stem cells engraft, give rise to mixed chimerism, and induce tolerance without space-creating treatment, e.g., without whole body irradiation and/or thymic irradiation. The number of donor hematopoietic cells administered can be at least twice, at least equal to, or at least 75, 50, or 25% as great as, the number of hematopoietic cells found in an adult. The number of donor hematopoietic stem cells administered to the recipient can be at least twice, at least equal to, or it least 75, 50, or 25% as great as, the number of hematopoietic stem cells found in an adult. The donor stem cells can be provided in two or more separate administrations.

The number of donor cells administered to the recipient can be increased by either increasing the number of stem cells provided in a particular administration or by providing repeated administrations of donor stem cells.

Repeated stem cell administration can promote engraftment, mixed chimerism, and preferably long-term deletional tolerance in graft recipients. Thus, the invention also includes methods in which multiple hematopoietic stem cell administrations are provided to a recipient, e.g., additional administrations other than an administration on the day of graft transplantation. Multiple administration can substantially reduce or eliminate the need for hematopoietic space-creating irradiation or chemotherapy. Administrations can be given prior to, at the time of, or after graft implantation. In preferred embodiments multiple administrations of stem cells are provided prior to the implantation of a graft. Two, three, four, five, or more administrations can be provided. The period between administrations of hematopoietic stem cells can be varied. In preferred embodiments a subsequent administration of hematopoietic stem cell is provided: at least two days, one week, one month, or six months after the previous administration of stem cells; when the recipient begins to show signs of host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells; or generally, as is needed to maintain a level of mixed chimerism sufficient to maintain tolerance to donor antigen. Stem cells may be administered either as unmanipulated, or manipulated bone marrow or mobilized peripheral blood stem cells. Such manipulation might include the positive selection of cells demonstrating a specific phenotype (i.e. the expression of an antigen such as CD34), or the negative selection of cells demonstrating undesirable phenotypes, such as certain populations of T-cells. In those embodiments where subsequent administration(s) of hematopoietic stem cells are given when the recipient begins to show signs of host lymphocyte response to donor antigen or when the level of chimerism decreases, only manipulated donor bone marrow or mobilized hematopoietic stem cells should be administered.

One or more post graft-implantation-administrations of donor stem cells can also be provided to minimize or eliminate the need for irradiation. Post graft administration of hematopoietic stem cell can provided: at least two days, one week, one month, or six months after the previous administration of stem cells; at least two days, one week, one month, six months, or at any time in the life span of the recipient after the implantation of the graft; when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells; or generally, as is needed to maintain tolerance or otherwise prolong the acceptance of a graft.

When multiple stem cell administrations are given one or more of the administrations can include a number of donor hematopoietic cells which is at least twice, is equal to, or is at least 75, 50, or 25% as great as, the number of bone marrow cells found in an adult of the recipient species; include a number of donor hematopoietic stem cells which is at least twice, is equal to, or is at least 75, 50, or 25% as great as, the number of bone marrow hematopoietic stem cells found in an adult of the recipient species.

Sources of Cells for Allogeneic Stem Cell Transplantation

Some methods described herein use hematopoietic stem cells, e.g., mobilized enriched peripheral blood hematopoietic stem cells, obtained directly from the donor. Other methods may require more hematopoietic cells than a donor can provide. Ex vivo expansion of hematopoietic stem cells can provide larger amounts of hematopoietic cells.

A living human donor can provide about $7.5 \times 10^8$ bone marrow cells/kg of recipient. Methods of the invention can include the administration of at least 2 or 3 times this number (per kg) and in some cases up to or at least 10, 15, or 20 times this number. The requisite numbers of bone marrow cells can be provided by the ex vivo expansion or amplification of human stem cells. Ex vivo expansion is reviewed in Emerson, 1996, Blood 87:3082, hereby incorporated by reference. Methods of ex vivo expansion are described in more detail in Petzer et al., 1996, Proc. Natl. Acad. Sci. USA 93:1470; Zundstra et al., 1994, BioTechnology 12:909; and WO 95 11692 Davis et al., all of which are hereby incorporated by reference. Sources of hematopoietic stem cells include bone marrow cells, mobilized peripheral blood cells, and, when available, cord blood cells. Donor peripheral hematopoietic stem cells are preferred in some methods.

Anti-CD2 Antibodies

Methods described herein include the administration of anti-CD2 monoclonal antibodies to the recipient. Anti-CD2 monoclonals suitable for use in the methods described herein can be made by generating a rodent monoclonal which is reactive with CD2 found on the surface of human lymphocytes and humanizing the rodent antibody. "Human" anti-CD2 made in a mouse or rat reconstituted with human immune system components can also be used.

Particularly preferred anti-CD2 monoclonals include those which bind an epitope which overlaps, or which is similar to, the epitope bound by rat monoclonal anti-CD2 antibody BTI-322 or the humanized anti-CD2 antibody, MEDI-507. For example, a preferred anti-CD2 antibody is one which can inhibit the binding of BTI-322 to its epitope, inhibit the binding of MEDI-507 to its epitope, be inhibited in binding to its epitope by BTI-322, or be inhibited in binding to its epitope by MEDI-507. BTI-322 is described in U.S. Pat. No. 5,817,311, hereby incorporated by reference. BTI-322 has been deposited with the ATCC as accession number HB 11423. MEDI-507 is described in PCT/US97/12645 (WO9903502, published Jan. 28, 1999), hereby incorporated by reference.

MEDI-507 is a humanized form of a rat IgG2b kappa monoclonal antibody raised against human lymphocytes and reactive with the CD2 antigen on the lymphocytes. MEDI-507 can be supplied as a solution in phosphate buffered saline (pH 7.4) in vials containing 15 mg for intravenous use.

MEDI-507 is described below. Although this description illustrates the functional characteristics of MEDI-507, other anti-CD2 antibodies with these functional properties can be used. The methods used to characterize MEDI-507 can applied to a candidate anti-CD2 antibody to determine if it has similar functional properties to MEDI-507, i.e., that it has one or more of the following properties: it binds to all human T cells and most NK (natural killer) cells (approximately 85% of peripheral blood mononuclear cells); it does not react nonspecifically with human tissues; it specifically reacts with tissue of lymphoid origin; it inhibits in vitro T cell proliferation in response to mitogens, antigens, or allogeneic stimulator cells, preferably at nanomolar concentrations; it can interfere with the proliferation of activated T cells, preferably even if added as late as three days after initiation of a five day mixed lymphocyte response (MLR); it does not induce proliferation, IL-2, or interferon-γ (IFN-γ) production in lymphocytes from the majority of human peripheral blood lymphocyte samples;

it results in the production of less tumor necrosis factor-α (TNF-α) than does OKT3; it inhibits IL-2, TNF-α, and IFN-γ production in response to OKT3 stimulation; it causes reversible modulation of the expression of CD2 on human peripheral blood lymphocytes in culture.

Specificity

MEDI-507 binds to all human T cells and most NK (natural killer) cells (approximately 85% of peripheral blood mononuclear cells). Immunohistochemistry was used to study the specificity of binding of MEDI-507 with human tissues. The study concluded MEDI-507 does not react nonspecifically with human tissues. Specific staining of tissues was observed only in those of lymphoid origin. This result supports the observed specificity of this antibody for the CD2 cell surface molecule.

Effect on Target Cells: Inhibitory Properties

MEDI-507 inhibits in vitro T cell proliferation in response to mitogens, antigens, and allogeneic stimulator cells at nanomolar concentrations and at concentrations similar to that of the rat parent antibody. MEDI-507 can interfere with the proliferation of activated T cells even if added as late as three days after initiation of a five day mixed lymphocyte response (MLR). Interaction of MEDI-507 with T cells in vitro during alloantigen activation results in alloantigen-specific anergy or hyporesponsiveness.

Effect on Target Cells: Activation

MEDI-507 is not an activating antibody. MEDI-507 does not induce proliferation, or IL-2 or interferon-γ (IFN-γ) production in lymphocytes from the majority of human peripheral blood lymphocyte samples. There is less tumor necrosis factor-α (TNF-α) produced in response to MEDI-507 than to OKT3 (a murine anti-CD3 antibody used for treatment of allograft rejection). MEDI-507 inhibits IL-2, TNF-α, and IFN-γ production in response to OKT3 stimulation.

Effect on Target Cells: CD2 Expression

MEDI-507 causes the modulation of the expression of CD2 on human peripheral blood lymphocytes in culture. This effect is reversible.

Pharmocokinetics and Pharmacodynamics

The pharmacokinetics and pharmacodynamics of MEDI-507 were investigated in chimpanzees under general inhalational anesthesia. MEDI-507 was administered as a single daily intravenous infusion over 30 minutes given every other day for three doses. A dose of 0.43 mg/kg was given except for the first animal who received a dose of 0.143 mg/kg for the first of the three doses. The highest daily dose administered was equivalent to a human dose of ~30 mg. There was a MEDI-507 treatment-related decrease in peripheral blood lymphocyte counts. This occurred following the initial dose and was sustained for three weeks, then gradually resolved, with total lymphocyte numbers returning to near baseline values by five weeks after dosing. Inhibition of MLR and NK activity was observed in all groups treated with MEDI-507. The results of lymph node biopsies taken from these chimpanzees following the three doses of MEDI-507 over six days of treatment revealed minimal depletion of lymphocytes in the paracortical areas of lymph nodes. Moderate first dose effects were observed in one of two chimpanzees treated as above, and in an additional chimp receiving a single dose of 0.143 mg/kg of MEDI-507 without steroid pre-medication. These consisted of hypertension, muscle spasms, brief apnea, rales, and apparent headache, and resolved over a period of 24 hours. No further clinical adverse events were observed in animals receiving additional doses without pre-medication. A second study of MEDI-507 in ketamine sedated chimpanzees that were not pre-medicated did not reveal these adverse effects, with doses of 0.6 mg/kg/day and 1.43 mg/kg/day for three consecutive days. Mild to moderate depletion of T cells in lymph nodes were observed in both dose groups at 7 and 11 days after the first dose, with recovery being 42-70 days after dosing. These results supplemented earlier studies in chimpanzees using BTI-322, the rodent parent antibody to MEDI-507. Doses of 0.143 mg/kg/day and 1.43 mg/kg/day for ten consecutive days resulted in depletion of lymphocytes in peripheral blood and lymph nodes biopsied on the day after dosing (Day 11). Depletion was more profound at the higher dose level and predominantly affected the T-cell regions of the lymph node in the paracortical regions, but left the germinal centers intact. Doses lower than these did not produce depletion of lymphocytes in lymph nodes, but did produce peripheral blood lymphocyte depletion. In a phase I study in newly transplanted renal allograft recipients, the estimated steady state alpha phase $t_{1/2}$ of MEDI-507 was 29 hours in the 0.06 mg/kg dose group at 49 hour in the 0.12 mg/kg dose group. Additional pharmacokinetics have been performed in patients receiving higher doses of MEDI-507, including a study in which MEDI-507 was administered at approximately 0.4 mg/kg. In this study, where the beta phase $t_{1/2}$ could be estimated, the beta elimination is approximately 6-10 days. Patients in the allograft study had received high dose steroids as part of the peri-transplant immunosuppressive regimen several hours prior to the first dose of MEDI-507; no adverse reactions or first dose effects after MEDI-507 administration were observed.

In methods described herein, high dose MEDI-507 immediately pre-transplant, as part of the conditioning regimen, will result in more complete T cell depletion than can be achieved with ATGAM, which has been used in the monkey models. Engraftment of donor hematopoietic progenitor cells for the induction of mixed chimerism requires a high degree of T-cell depletion in the recipient. The dose and dosing regimen of MEDI-507 chosen for use in this protocol were based on the extent of T-cell depletion in lymph nodes and blood in studies in chimpanzees.

Safety and Efficacy

Safety and preliminary efficacy data on the use of BTI-322, the rodent monoclonal antibody parent to the humanized antibody MEDI-507, have been derived from more than 130 patients in the US and Europe who have been treated with BTI-322 at doses up to 10 mg/day for up to 20 days, for several indications, including prevention and treatment of solid organ allograft rejection, and for the treatment of steroid resistant acute GvHD. Aside from modest first dose reactions in some patients receiving BTI-322, which have been easily controlled and confined to the first dose, this agent has generally been well tolerated, and no apparent increase in infections or malignancies in treated patients, some of whom have been followed for four years, has been noted up to the present time. In limited studies of renal allograft recipients receiving MEDI-507 at doses up to 0.12 mg/kg, no first dose symptoms were observed. One patient receiving MEDI-507 with no steroid pre-medication for treatment of psoriasis experienced a mild/moderate first dose reaction.

Preparation, Formulation, and Storage of MEDI-507

The antibody is produced by in vitro culture of hybridoma cells in a protein-free medium. The crude antibody is purified by a combination of anion exchange, cation exchange and hydrophobic interaction, and size exclusion chromatography. The purified bulk product is released based on the results of in vitro potency tests, purity and identity tests, and the absence of fungi, bacteria, mycoplasma and virus contaminants. The final antibody product is vialed as a solution in phosphate buffered saline (pH 7.4) containing no preservatives or other excipients. Each vial contains 15 mg of antibody in a volume of 4 mL.

Recovery and Enrichment of Peripheral Blood Hematopoietic Progenitor Cells

Methods described herein can use mobilized peripheral blood hematopoietic stein cells. It is generally desirable to enrich such peripheral cell preparations for $CD34^+$ cells. Buoyant density separation can be used to enrich the desired cells The enrichment system should result in a preparation in which $CD34^+$ cells are enriched as compared with red blood cells, granulocytes, and T cells.

The enrichment process provides for the recovery and enrichment of hematopoietic progenitor cells obtained by leukapheresis of peripheral blood after cytokine mobilization. This cell population is capable of engraftment and complete hematologic reconstitution of lethally irradiated patients with malignancies undergoing bone marrow transplantation. Buoyant density based enrichment can provide for the production of a more consistent cell product for infusion, for increasing the viability of progenitor cells after cryopreservation, and for permitting the infusion of hematopoietic progenitor cells with a reduced risk for the development of acute graft vs. host disease in the recipient.

A cell separation kit which includes several medical grade plasticware components and a bottle of buoyant density solution (BDS), a sterile non-pyrogenic density medium which can be formulated at different densities to fractionate different cell types from blood, marrow, and other somatic tissues based on their buoyant density can be used for the enrichment process. The buoyant density solution has an optimum density (1.0605 g/mL) for the isolation of hematopoietic stem cells ($CD34^+$ cells) from cytokine-mobilized peripheral blood.

The DENDREON™ 300 System is suitable for use with methods described herein.

Patient Selection

Although the methods described herein are generally applicable to human recipients, in preferred embodiments the recipients should have one or more, and preferably all, of the characteristics described below. The patient and donor profiles discussed below are provided as an example and are not limiting. The methods described herein can be performed on patients (and donors) which do not fit these criteria.

Preferably, patients should be receiving a first or second transplant, which should, but does not have to be, a living donor renal allograft. The donor-recipient pair should have HLA specificities such that detection of chimerism by flow cytometry using anti-HLA antibodies is possible. Both the current and historical PRA for the current allograft should be <20%. Patients should not have received any thymic irradiation therapy in the past, and should not have a contraindication to radiation therapy. The donor should be capable of undergoing cytokine-mediated progenitor cell mobilization and leukapheresis, as well as serving as the kidney donor. Patients should have received one dose of a currently recommended pneumococcal vaccine, and *H. influenzae* type b conjugate vaccine at least four weeks prior to the transplant. The donor-recipient pair should have at least one HLA antigen difference detectable by flow cytometry using anti-HLA antibodies, to permit assessment of donor chimerism.

More detailed inclusion and exclusion criteria for preferred embodiments are presented below.

Inclusion Criteria

1. Patients (male or female) must not be less than 18 years of age nor more than 55 years of age.
2. Patients must be undergoing a first or second transplant, which must be a living donor renal allograft, and may have had either a living donor or a cadaveric transplant as the first transplant.
3. Patients with a relative contraindication to standard transplantation, either related to prior non-compliance with the immunosuppressive regimen, underlying disease, or other reasons, will be preferred patients for this protocol.
4. Women and men must be willing to use adequate contraception, as determined by the investigator, for the first six months after renal transplantation.
5. The patient or his/her guardian and the transplant donor must voluntarily sign informed consent forms for entry into this study after the contents of those documents have been fully explained to them.
6. The kidney donor must be capable of undergoing cytokine mediated peripheral progenitor cell mobilization and leukapheresis.
7. The recipient must have received a currently recommended pneumococcal vaccine and *Hemophilus influenzae* type b-conjugate vaccine at least 4 weeks prior to transplantation.
8. The patient must be capable of complying with the schedule of study visits, especially after discontinuation of cyclosporine.

Exclusion Criteria

1. Patients receiving an ABO blood group incompatible renal allograft.
2. Patients with a current or historical PRA >20%, and if a second allograft recipient must be at least one year post-graft loss from that initial transplant.
3. Patients who are leukopenic (WBC less than $2000/mm^3$) or thrombocytopenic (platelet count<$100,000/mm^3$).
4. Patients who are seropositive for HIV-1 or HBsAg, or sero-negative for Hepatitis C virus with a Hepatitis C virus sero-positive donor
5. Patients in heart failure or pulmonary edema.
6. Lactating or pregnant women. Women must have a negative serum pregnancy test prior to study entry.
7. Patients with a history of cancer.
8. Patients with a contraindication to the long-term administration of cyclosporine post-transplant.
9. Patients who have received radiation therapy in the past.
10. Patients with a known genetic disease or family history that may result in greater sensitivity to the effects of irradiation, or physical deformity that would preclude adequate shielding or appropriate dosing during the irradiation component of the conditioning regimen.
11. Patients or their donors who are, in the opinion of the investigator, not capable of giving informed consent for the study, either because of a language barrier or for any other reason.

Patient Care, Evaluations, and Surgical Methods

A complete physical examination of both the donor and recipient should be performed. The results of the physical exam performed on the donor during the pre-transplant evaluation process may be used in lieu of a new exam, if there has been no notable change in the donor's physical condition. Abnormalities noted on physical examination of the patient and donor should be recorded.

The surgical techniques related to the renal transplant and (optional) splenectomy can be accomplished according to the surgeon's clinical judgement and experience using standard techniques. Procedures performed on the donor, including cytokine mobilization of peripheral blood progenitor cells and leukapheresis are described herein, but the donor nephrectomy should be accomplished according to the surgeon's clinical judgement and experience.

Recipients should be evaluated during the first three weeks post-transplant for the acute safety and tolerability of the conditioning regimen, including evaluation for neutropenia, thrombocytopenia, lymphopenia and nausea as well as acute side effects that may be associated with anti-CD2 antibodies, e.g., MEDI-507. The occurrence of other opportunistic and invasive bacterial infections and malignancies should be assessed at 3 and 6 months, and, 1 and 2 years post-transplant. Allograft rejection, renal function, graft vs. host disease, and graft and patient survival, will be assessed at 1, 3, 6, 12, and 24 months post-transplant. The allograft donor will undergo hematologic assessment following the progenitor cell mobilization procedures at 1, 3, 6, and 12 months post-donation, an assessment of the tolerability and safety of the G-CSF treatment, and renal function.

Evaluation of donor cell chimerism by flow cytometry should be done pre-transplant, and at 1, 3, 7, 10, 14, 21, 28, 42, and 56 days post-transplant in transplant recipients. If chimerism is still present at 56 days, patients should be evaluated every 30 days thereafter for persistence of chimerism, until no longer detectable, or until one year post-transplant. Peripheral blood lymphocyte subsets should be evaluated at the same time points. A lymph node biopsy should be taken from the renal bed at the time of transplantation, and assessed by routine histology, by immunohistochemistry, and by flow cytometry for lymphocyte subsets. Mixed lymphocyte reaction (MLR) should be performed at baseline, and every 3 months for one year post-transplant, using irradiated frozen donor lymphocytes as stimulator cells, and using stored pooled third party lymphocytes as control stimulator cells, respectively, with recipient lymphocytes as responders.

Kits

Kits for use with methods described herein are provided. A kit will include the supplies necessary for the conditioning of one patient, including materials for buoyant density separation of hematopoietic stem cells, e.g., a DENDREON™ 300 System, and a supply of anti-CD2 humanized monoclonal antibody, e.g., MEDI-507 monoclonal antibody. The two components of the kit require different storage conditions, the materials for cell separation at room temperature (20-25° C.), and monoclonal antibody at 2-8° C. Kits will be assigned to specific patients. No component of any kit should be exchanged between kits, and kits may not be exchanged between patients.

EXAMPLE 1

Allogeneic Transplantation with Whole Body Irradiation and Thymic Irradiation

Methods described include a series of procedures and treatments including total body and thymic irradiation, antibody administration, hematopoietic progenitor cell infusion, and splenectomy.

The renal allograft recipient will receive:
300 cGy (150 cGy on each of two successive days) of whole body irradiation;
700 cGy of thymic irradiation;
one or more doses (preferably, four doses) of an anti-CD2 monoclonal antibody, e.g., MEDI-507, on days −4, −3, −2, −1, at a dose of 0.1 mg/kg on day −4 and of 1.0 mg/kg on days −3, −2, and −1, (this can be preceded by 1-4 hours by a single intravenouse dose of methylprednisolone sodium succinate, 8 mg/kg, to a maximum dose of 500 mg);
a splenectomy on the day of transplantation day 0;
donor peripheral blood progenitor cells will be infused on the day of transplantation day 0; and
a 42-day course of cyclosporine started on the day prior to transplantation.

The regimen begins six days prior to the day of transplantation, which is designated Day 0. Days pre-transplant are designated by negative numbers in descending order, while days post-transplant are designated by positive numbers in ascending order.

The method is described in more detail below.

Cytokine Mobilization of Hematopoietic Progenitor Cells and Leukapheresis of the Donor Renal donors will undergo treatment with recombinant human G-CSF (filgrastim), 6-10 micrograms/kg/day subcutaneously for 5-7 days to mobilize hematopoietic progenitor cells into the peripheral blood where they will be collected by a 3-4 blood volume (15-18 L) leukapheresis using the standard techniques. Cytokine mobilization should be monitored, and the day of leukapheresis will be determined, by the $CD34^+$ cell count and total white blood cell count in peripheral blood. The leukapheresis product should then be further processed by separating hematopoietic cells by buoyant density, e.g., by using a system such as the DENDREON™ 300 System, then cryopreserved until needed for infusion into the recipient at the time of transplantation. In one embodiment, cells may be cryopreserved with 4% human serum albumin using 10% dimethylsulfoxide (DMSO) with controlled rate freezing. In another embodiment, an appropriate amount of donor plasma may be used in lieu of human serum albumin. A minimum of $2 \times 10^8$ cells/kg, containing at least $5 \times 10^6$ $CD34^+$ cells/kg after processing are required, and if necessary may require more than one leukapheresis procedure to be performed. The procedure used is similar to that used for autologous or allogeneic progenitor cell transplantation. Cytokine treatment and leukapheresis should be completed no less than two weeks prior to the transplant to provide adequate time for hematologic recovery and return to baseline status prior to renal donation. The total WBC count of the donor should not exceed $70 \times 10^3/mm^3$. If this level is reached, the dose of filgrastim should be reduced and the WBC count followed daily until it falls below this value. Every effort should be made to collect an adequate cell product from these patients, however, unless clinically contraindicated.

Cytokine Mobilization of Hematopoietic Progenitor Cells and Leukapheresis of the Recipient The same procedure as outlined for the donor will be performed on the recipient at least 2 weeks prior to transplantation to store frozen progenitor cells that will be available in case of slow recovery of hematopoiesis following administration of the conditioning regimen. In this case, $2\times10^6$ CD34+ cells/kg will be stored. Buoyant density purification is not required for this cell product. The decision to use these cells for reconstitution of the recipient will be based on the clinical judgement of the investigator and his local hematology consultant, in consultation with the study medical monitor.

Buoyant Density Based Enrichment of Progenitor Cells

Hematopoietic cells should be enriched by a buoyant density-based method. Colloidal silica solution (1.0605 g/mL) (BDS 60) formulated for the recovery, at the density interface, of CD $34^+$ cells from peripheral blood should be used. This material has not been formulated for the recovery of CD $34^+$ cells from bone marrow, and thus, can only be used for recovery of progenitor cells from blood after cytokine mobilization. A kit, such as the DENDREON™ 300 System, which includes sterile, centrifugation and washing containers and tubing that allow processing of cells in a closed manner, can be used in the enrichment process. A plastic insert in the separation container facilitates the trapping of unwanted cells below the density interface where the CD $34^+$ cells are recovered. All cell processing must be done using sterile technique under aseptic conditions in a properly equipped laboratory with experience in the preparation of hematopoietic progenitor cells for human progenitor cell and bone marrow transplantation. The procedure outlined below is to be followed for the preparation of donor cells for infusion. The cells are separated at about 850 g. Sample treatment is as follows:

Sample Preparation

Use the mobilized apheresis product. If anticoagulant is necessary, an anticoagulant such as Anticoagulant Citrate Dextose USP formula A (ACD-A) may be used. Determine the number of nucleated cells and hematocrit on an aliquot of the product. Centrifuge the product to remove plasma and resuspend the pellet in 250 mL of 0.9% saline (Ca, Mg free). The maximum number of nucleated cells per device is $5\times10^{10}$ cells, with a hematocrit of no greater than 15%.

Device Preparation (The following instructions are provided for use with the DENDREON™ 300 System or similar devices. Other devices can be used as well, though the exact protocol may differ.)

Shake the bottle of BDS60 solution to mix the contents well. Using tubing set A, connect the separation device to the bottle of BDS60.

Use tubing set b to connect the apheresis bag to the device.

Open the separation container air vent.

Fill the lower chamber just to the top of the insert with BDS60 colloidal silica solution.

Tilt the device by about 1 cm with the vent side up and fill the upper chamber with 250 mL of the cell suspension. Do not fill the chamber to above the fill line on the side.

Finish filling the chamber with the remaining colloidal silica solution by underlaying below the cell suspension through port A, and close the air vent after removing all the tubing.

Disconnect the tubing sets, and centrifuge the chamber at 850 g for 30 minutes at ambient temperature (18-22° C.). Do not use the brake on the centrifuge.

Harvest the Cells (The following instructions are provided for use with the DENDREON™ 300 System or similar devices. Other devices can be used as well, though the exact protocol may differ.)

Open the Separation Container air vent upon removal from the centrifuge. Connect a tubing set between red port B on the separation chamber and white port C on the Wash Container.

Invert the separation container. Open the clamp of the tubing and the air vent of the wash container and fill the wash container. Do not exceed the fill line on the side of the chamber. Disconnect the tubing and close the air vent on the Separation Container and the Wash Container.

Wash the Cells (The following instructions are provided for use with the DENDREON™ 300 System or similar devices. Other devices can be used as well, though the exact protocol may differ.)

Wash the cells using a conical centrifuge bucket adapter.

Centrifuge the wash container at 850 g for 15 minutes at ambient temperature. Using a new Tubing Set connected to white port C, and opening the air vent, invert and drain the supernatant.

Using a new Tubing Set connect a bag of 0.9% saline (Ca, Mg free) to the Wash Container, and fill to the fill line. Disconnect the tubing, close the port, and air vent, and resuspend the pellet by inversion and using a vortex mixer.

Immediately centrifuge the cell suspension at 550 g for 10 minutes at ambient temperature. Do not use the brake.

Attach Tubing set C and drain the supernatant. Remove and discard the tubing.

Pellet Recovery (The following instructions are provided for use with the DENDREON™ 300 System or similar devices. Other devices can be used as well, though the exact protocol may differ.)

Use a 60 cc syringe to deliver a specified volume of culture medium to the Wash Container.

Close the port and swirl the Wash Container to resuspend the cells.

Attach Tubing Set B to the Container and drain the cell suspension into a storage bag.

Cryopreservation of the CD34$^+$ Cell Preparation

The CD34+ enriched cell product should be cryopreserved using 10% DMSO with 4% human serum albumin and controlled rate freezing. Cells are then transferred to the vapor phase of a liquid $N_2$ freezer until used. Three smaller aliquots of cells should also be cryopreserved for subsequent CFU assays.

Characterization of the Leukapheresis Product

The leukapheresis product should be characterized as to the total volume, hematocrit, total nucleated cell content, total CD3+ T-cell content, and total CD34+ cell content, as well as CFU-GM content, at the time of harvest, prior to enrichment by buoyant density. These same tests should be performed on the cell product harvested from the density interface prior to cryopreservation. If more than one leukapheresis is performed, these tests should be done on each harvest. In addition, aliquots of cells from the original and post-buoyant density processed material should be tested for sterility, and the results of such tests obtained prior to infusion of cells into the recipient.

Whole Body Irradiation (Days −6 and −5)

The 300 cGy dose of whole body irradiation (WBI) is administered in 2 fractions of 150 cGy each, on 2 successive days (Days −6 and −5). Patients will be premedicated, e.g., with odansetron hydrochloride (Zofran) 32 mg IV over 30 min. prior to each days irradiation, and as needed after irradiation to treat nausea. Patients will be irradiated using an AP/PA approach while lying supine on the table. Two fields will be used, with matching at the umbilicus. The upper field will have its upper border just below the orbit, and the lower field will have its lower border at the knees. The dose will be calculated at the midplane at the umbilicus. A 6 MV machine is optimal, but energies of 4-10 MV can be used, the latter with beam spoiling. The dose rate used will be the maximum permitted by the machine, unless a dedicated WBI machine is available to administer a dose rate of 10 cGy per minute, in which case that machine should be used. In men the testes will be shielded. Women will be offered the option for laparoscopic clipping and fixing of one ovary to permit shielding. No lung shielding will be used. The details regarding the field sizes, dose calculation, energy, beam spoiling, and dose rate will be recorded on the CRF.

Thymic Irradiation (Day −1)

700 cGy of thymic irradiation can be administered in a single dose on Day −1. A field size of approximately 8 cm wide and 10 cm in longitudinal dimension should be used, with the midpoint of the upper edge of the field at the sternal notch. The dose should be calculated at a depth of approximately 6 cm, guided by results of a lateral chest roentgenogram for the approximate location of the thymus. A 10 MV machine at maximum dose rate should be used. No premedication for nausea should be required. The details regarding the field sizes, dose calculation, energy, beam spoiling, and dose rate will be recorded on the CRF.

Administration of Anti-CD2 monoclonal antibody (Days −4, −3, −2, and −1)

The first dose of anti-CD2 monoclonal antibody, e.g., MEDI-507, which may be administered on Day −4, or prior to that, e.g., Day −7, should be 0.1 mg/kg, administered over 30 minutes, and preceded, by 1-4 hours, by the administration of intravenous methylprednisolone sodium succinate, 8 mg/kg up to a maximum dose of 500 mg, along with diphenhydramine 50 mg p.o., and acetaminophen, 650 mg, p.o. The second (and subsequent, if any) doses (Days −3, −2 and −1) should be 1 mg/kg, administered over 2 hours, without steroid pre-medication. Diphenhydramine and acetaminophen may be administered prior to the second and subsequent doses, however.

The prepared 0.1 mg/kg and 1 mg/kg doses of monoclonal antibody should be supplied from the pharmacy to the person who will administer the drug. For the first dose (0.1 mg/kg), monoclonal antibody should be administered over 30 minutes using an infusion pump. The solution should be prepared to a final concentration of 0.1-0.3 mg/mL (30-100 mL). Subsequent doses are 1 mg/kg. These doses should be administered over 2 hours at a permissible concentration of 0.3-1.8 mg/ML (50-100 mL infusion volume), using an infusion pump.

The actual start and stop times of antibody administration, should be recorded on the appropriate case report form. Drug doses should be administered at the same time each day, so that there are 24 hours between doses. Antibody should be administered several hours after dialysis, if possible.

Since compatibility with other intravenously administered medications is not known, the monoclonal antibody solutions should not be infused through a common intravenous line used for other medications, unless the line is flushed prior to and after administration of the monoclonal antibody.

MEDI-507 Preparation (The following instructions are provided for MEDI-507. Other anti-CD2 antibodies can be used, though the exact protocol may differ.)

1. Bring an appropriate number of vials for each dose to room temperature (approximately 30 minutes) The number of vials supplied in each patient-specific kit are appropriate for the patient's weight. One vial is needed for the 0.1 mg/kg dose on the first dosing day (Day −7 or Day −4).

TABLE 0-1

Number of vials needed for 1 mg/kg doses.

| Patient Weight | # Vials per dose | Total Dose |
|---|---|---|
| <40 kg | 2 | 30 mg |
| 41-50 kg | 3 | 45 mg |
| 51-60 kg | 4 | 60 mg |
| 61-80 kg | 5 | 75 mg |
| 81-100 kg | 6 | 90 mg |

2. Inspect each vial visually for precipitate and discoloration. If there is precipitate and/or discoloration, do not use the vial.

3. Preparation of MEDI-507 for Injection

One vial (15 mg in 4 mL) is required for the first dose of MEDI-507 (0.1 mg/kg). Once the appropriate volume is removed, the remaining MEDI-507 must be discarded, after appropriate drug accountability information is completed. The appropriate volume of MEDI-507 should be removed using a 10 mL syringe through a sterile low protein binding filter (0.2 micrometers pore size) using aseptic technique. Discard the filter. Dilute the antibody solution to a final volume of 30-100 mL in a syringe pump for infusion. Steroid premedication (see above, and Section 10) is required prior to administration of the first dose, which is infused over 30 minutes. For subsequent doses draw the required total volume of antibody solution into a 60 mL syringe through a sterile low protein binding filter (0.2 micrometer pore size) using aseptic technique. Discard the filter. Dilute the antibody solution to a final volume of 50-100 mL in the IV infusion bag or syringe pump. The 50-100 mL volume of the MEDI-507 solution is infused over 2 hours. Pre-medication with 650 mg of acetaminophen and 50 mg of diphenhydramine may precede administration of MEDI-507 by two hours. This procedure should be followed for each of the subsequent MEDI-507 infusions.

Donor Progenitor Cell Infusion, Splenectomy and Renal Transplantation (Day 0)

Donor progenitor cells are thawed and prepared for infusion according to standard procedures. The performance of a splenectomy is optional prior to the renal transplant and progenitor cell infusion, according to standard surgical techniques. If the splenectomy is performed, the spleen should be sent for routine histopathology, and both immunofluorescence and flow cytometry evaluations. The renal transplant is performed according to standard surgical techniques, preferably using an iliac fossa, extraperitoneal approach and utilizing a ureteropyelostomy with the recipient ureter if surgically feasible.

Administration of an Immunosupressant, e.g., Cyclosporine, and Use of Corticosteroids Cyclosporine, either Neoral® or Sandimmune® or equivalent should be administered orally starting on Day −1. The initial dose should be 6 mg/kg given twice, approximately 12 hours apart, followed by a single dose of 4 mg/kg given late in the evening on the day of transplantation (Day 0). Starting on the day after transplantation (Day 1), the dose should be 4 mg/kg given twice a day, and adjusted to provide a trough whole blood concentration of 400-500 ng/mL, as measured by a monoclonal antibody based assay, or the equivalent if a different assay or serum rather than whole blood are used, to determine trough cyclosporine concentrations. Cyclosporine should be continued for 35 days, then tapered over 7 days and discontinued on Day 42, if criteria for cyclosporine are not met.

In order to further protect the patient from possible allograft rejection post-transplant, oral prednisone (or an equipotent dose of methyl prednisone) should be administered starting on Day 22, if the patient has not exhibited ≧1% lymphocytic chimerism at any time during the preceding 21 days post-transplant. The dose of prednisone will be 0.5 mg/kg once daily from Days 22-42, then tapered to 0.1 mg/kg. Because corticosteroids may interfere with the induction of tolerance, steroids should only be administered under circumstances outlined here. Patients administered steroids would not be eligible for cyclosporine withdrawal, and so will continue on this regimen indefinitely.

Discontinuation of the Immunosupressant

Patients will be considered for the discontinuation of cyclosporine at Day 42 post-transplant if they meet the following criteria:
1. No clinically significant acute allograft rejection prior to this date.
2. The prior demonstration of donor lymphocytic chimerism at a level of 1% or greater in peripheral blood.
3. Adequate renal function as assessed by serum creatinine <2.5 mg/dl at day 35, and not varying by more than 20% for 1 month preceding Day 42, unless clearly related to a known cause of renal dysfunction such as cyclosporine toxicity, a urologic complication, other drug toxicity, etc.

Patients will be followed intensively for evidence of allograft rejection following discontinuation of cyclosporine. Serum creatinine will be measured every other day for the first two weeks after discontinuation, then twice a week for one month, then once a week for one month. Measurements will then be done once every two weeks for the remainder of the first year, then according to the routine post-transplant care prescribed to all allograft recipients Clinical Laboratory Tests Baseline clinical laboratory tests should be done within 24 hours prior to initiation of the conditioning regimen (Day −6) for the recipient. Two baseline hematologic evaluations will be done on successive days (these follow by about two weeks the completion of the mobilization and leukapheresis of the recipient). The hematology, tests should include: RBCs, WBCs with differential, hemoglobin, hematocrit, and platelet count. Blood chemistry should include: ALT, AST, BUN, serum creatinine, blood glucose, bilirubin, albumin, total protein, and potassium; and tests for anti-CD2 monoclonal antibody, e.g., MEDI-507 antibodies.

Baseline Immunologic Assessment of the Recipient

Lymphocyte subsets should be evaluated on 2 successive days, as for the hematologic evaluation, at least two weeks after completion of cytokine mobilization and leukapheresis. Mixed Lymphocyte Reaction (MLR) with donor and 3rd party stimulator cells should be performed.

Evaluation of the Transplant Donor

Baseline clinical laboratory tests must be done prior to the infusion of the first dose of filgrastim for mobilization of progenitor cells. The donor will, in addition, have daily CBCs and $CD34^+$ cell counts during cytokine mobilization. A further hematologic assessment of the donor should be performed on the day prior to start of conditioning of the recipient to assure that donation will be possible on the designated day. Tests should include: Hematology: RBC's, hemoglobin, hematocrit, WBCs with differential and platelet count; and Blood Chemistry: ALT, AST, BUN, creatinine, blood glucose, bilirubin, albumin, total protein and potassium.

Creating Hematopoietic Space by Administering to a Recipient One or More Chemotherapeutic Agents Hematopoietic space can be created, in the absence of irradiation, by administering to a recipient one or more chemotherapeutic agents, e.g., cyclophosphamide, busulfan, fludararabine, or any combination thereof. Preferably, one or more of the chemotherapeutic agents has a radiomimetic mechanism of action (i.e. interacts with DNA in a mechanism similar to ionizing radiation). In one embodiment, a single-agent chemotherapeutic regimen is administered. For example, cyclophosphamide can be administered preferably, intravenously) at a dose of 50 mg/kg/day for three consecutive days (e.g., cyclophosphamide can be administered on days −5, −4 and −3 prior to administration of stem cells or bone marrow on day 0). Alternatively, a combination of agents, e.g., cyclophosphamide, busulfan and/or fludararabine, can be used. The combination of agents can be administered sequentially or concurrently. Preferably, the combination is administered concurrently. Preferably, the cyclophosphamide is administered intravenously.

EXAMPLE 2

Allogeneic Transplantation with Thymic Irradiation and High Dose Donor Hematopoietic Stem Cell Administration Methods described include a series of procedures and treatments including thymic irradiation, antibody administration, high dose hematopoietic progenitor cell infusion, and splenectomy. Unless otherwise specified the methods are the same or analogous to those used in Example 1.

The renal allograft recipients (which do not receive whole body irradiation) receive:

approximately 1,000 cGy of thymic irradiation;

single or repeated (e.g., four) doses of an anti-CD2 monoclonal antibody, e.g., MEDI-507, prior to transplantation, e.g., on days −4, −3, −2, −1, at, e.g., a dose of 0.1 mg/kg on day −4 and of 1.0 mg/kg on days −3, −2, and −1, (optionally to be preceded by 1-4 hours by a single intravenouse dose of methylprednisolone sodium succinate, 8 mg/kg, to a maximum dose of 500 mg);

an optional splenectomy on day 0;

the administration of a high dose of donor peripheral blood progenitor cells on day 0;

optionally, a 42-day course of cyclosporine started on the day prior to transplantation.

The regimen begins six days prior to the day of transplantation, which is designated Day 0. Days pre-transplant are designated by negative numbers in descending order, while days post-transplant are designated by positive numbers in ascending order. The method is described in more detail below.

Cytokine Mobilization of Hematopoietic Progenitor Cells and Leukapheresis of the Donor Hematopoietic Progenitor Cells for Use in this Step can be Produced by In Vitro Expansion of Mobilized Peripheral Progenitor Cells.

Cytokine Mobilization of Hematopoietic Progenitor Cells and Leukapheresis of the Recipient At least 2 weeks prior to transplantation, recipient hematopoietic stem cells are mobilized to store frozen progenitor cells that will be available in case of slow recovery of hematopoiesis following administration of the conditioning regimen. This can be performed essentially as described in Example 1 above.

Buoyant Density Based Enrichment of Progenitor Cells

The step is similar to the analogous step in Example 1.

Cryopreservation of the $CD34^+$ Cell Preparation

The CD34+ enriched cell product may be cryopreserved with 4% human serum albumin (or an appropriate amount of donor plasma) using 10% dimethylsulfoxide (DMSO) with controlled rate freezing. Cells are then transferred to the vapor phase of a liquid $N_2$ freezer until used. Three smaller aliquots of cells should also be cryopreserved for subsequent CFU assays.

Characterization of the Stem Cell Preparation

The stem cell preparation should be characterized as to the total volume, hematocrit, total nucleated cell content, total CD3+ T-cell content, and total CD34+ cell content, as well as CFU-GM content, at the time of harvest, prior to enrichment by buoyant density.

Whole Body Irradiation

The use of a higher level of thymic irradiation and a higher level of donor hematopoietic stem cells eliminates the need for whole body irradiation.

Thymic Irradiation (Day −1)

1,000 cGy of thymic irradiation can be administered in a single dose on Day −1. A field size of approximately 8 cm wide and 10 cm in longitudinal dimension should be used, with the midpoint of the upper edge of the field at the sternal notch. The dose should be calculated at a depth of approximately 6 cm, guided by results of a lateral chest roentgenogram for the approximate location of the thymus. A 10 MV machine at maximum dose rate should be used. No premedication for nausea should be required. The details regarding the field sizes, dose calculation, energy, beam spoiling, and dose rate will be recorded on the CRF.

Administration of Anti-CD2 Monoclonal Antibody (Days −4, −3, −2, and −1)

The first dose of anti-CD2 monoclonal antibody, e.g., MEDI-507, (Day −4) should be 0.1 mg/kg, administered over 30 minutes, and preceded, by 1-4 hours, by the administration of intravenous methylprednisolone sodium succinate, 8 mg/kg up to a maximum dose of 500 mg, along with diphenhydramine 50 mg p.o., and acetominophen, 650 mg, p.o. The second and subsequent doses (Days −3, −2 and −1) should be 1 mg/kg, administered over 2 hours, without steroid pre-medication. Diphenhydramine and acetominophen may be administered prior to the second and subsequent doses, however.

In general, the administration is similar to that described above in Example 1. Optionally, one or more additional doses of anti-CD2 antibody can be administered.

High Dose Donor Progenitor Cell Infusion, Splenectomy and Renal Transplantation (Day 0)

Donor progenitor cells are thawed and prepared for infusion according to standard procedures. An optional splenectomy may be performed prior to the renal transplant and progenitor cell infusion, according to standard surgical techniques. If the spleen is removed, it is spleen is sent for routine histopathology, and both immunofluorescence and flow cytometry evaluations. The renal transplant is performed according to standard surgical techniques, preferably using an iliac fossa, extraperitoneal approach and utilizing a ureteropyelostomy with the recipient ureter if surgically feasible.

Administration of an Immunosupressant, e.g., Cyclosporine, and Use of Corticosteroids This step is optional. An immunosupressant, e.g., cyclosporine, is administered essentially as described in Example 1.

Discontinuation of the Immunosupressant

Discontinuation criteria are similar to those discussed in Example 1.

Clinical laboratory tests, baseline immunologic assessment of the recipient, evaluation of the transplant donor are performed essentially as is described in Example 1.

EXAMPLE 3

Allogeneic Transplantation with High Dose Donor Hematopoietic Stem Cell Administration and Blockade of Costimulation Methods described include a series of procedures and treatments including antibody administration, high dose hematopoietic progenitor cell infusion, blockade of costimulation, and splenectomy. Unless otherwise specified the methods are the same or analogous to those used in Examples 1 and 2.

Donor renal allograft recipients (which do not receive whole body or thymic irradiation) receive:

repeated (e.g., four) doses of an anti-CD2 monoclonal antibody, e.g., MEDI-507, prior to transplantation, e.g., on days −4, −3, −2, −1, at, e.g., a dose of 0.1 mg/kg on day −4 and of 1.0 mg/kg on days −3, −2, and −1, (optionally to be preceded by 1-4 hours by a single intravenouse dose of methylprednisolone sodium succinate, 8 mg/kg, to a maximum dose of 500 mg;

a splenectomy on day 0;

the administration of a high dose of donor peripheral blood progenitor cells;

administration of an agent which blocks costimulation; optionally, a 42-day course of cyclosporine on the day prior to transplantation.

The regimen begins six days prior to the day of transplantation, which is designated Day 0. Days pre-transplant are designated by negative numbers in descending order, while days post-transplant are designated by positive numbers in ascending order. The method is described in more detail below.

Cytokine Mobilization of Hematopoietic Progenitor Cells and Leukapheresis of the Donor Hematopoietic Progenitor Cells for Use in this Step can be Produced by In Vitro Expansion of Mobilized Peripheral Progenitor Cells.

Cytokine Mobilization of Hematopoietic Progenitor Cells and Leukapheresis of the Recipient At least 2 weeks prior to transplantation, recipient hematopoietic stem cells are mobilized to store frozen progenitor cells that will be available in case of slow recovery of hematopoiesis following administration of the conditioning regimen. This can be performed essentially as described in Example 1 above Buoyant Density Based Enrichment of Progenitor Cells The step is similar to the analogous step in Example 1.

Cryopreservation of the $CD34^+$ Cell Preparation

The CD34+ enriched cell product may be cryopreserved with 4% human serum albumin (or an appropriate amount of donor plasma) using 10% dimethylsulfoxide (DMSO) with controlled rate freezing. Cells are then transferred to the vapor phase of a liquid $N_2$ freezer until used. Three smaller aliquots of cells should also be cryopreserved for subsequent CFU assays.

Characterization of the Stem Cell Preparation

The stem cell preparation should be characterized as to the total volume, hematocrit, total nucleated cell content, total CD3+ T-cell content, and total CD34+ cell content, as well as CFU-GM content, at the time of harvest, prior to enrichment by buoyant density.

Whole Body Irradiation

The use of a higher level of donor hematopoietic stem cells and costimulatory blockade allow whole body irradiation to be omitted from the method.

Thymic Irradiation (Day −1)

The use of a higher level of donor hematopoietic stem cells and costimulatory blockade allow thymic irradiation to be omitted from the method.

Administration of Anti-CD2 Monoclonal Antibody (Days −4, −3, −2, and −1)

The first dose of anti-CD2 monoclonal antibody, e.g., MEDI-507, (Day −4) should be 0.1 mg/kg, administered over 30 minutes, and preceded, by 1-4 hours, by the administration of intravenous methylprednisolone sodium succinate, 8 mg/kg up to a maximum dose of 500 mg, along with diphenhydramine 50 mg p.o., and acetominophen, 650 mg, p.o. The second and subsequent doses (Days −3, −2 and −1) should be 1 mg/kg, administered over 2 hours, without steroid pre-medication. Diphenhydramine and acetominophen may be administered prior to the second and subsequent doses, however.

In general, the administration is similar to that described above in Example 1. Optionally, one or more additional doses of anti-CD2 antibody can be administered.

Donor Progenitor Cell Infusion, Splenectomy and Renal Transplantation (Day 0)

Donor progenitor cells are thawed and prepared for infusion according to standard procedures. An optional splenectomy may be performed prior to the renal transplant and progenitor cell infusion, according to standard surgical techniques. If removed, the spleen can be sent for routine histopathology, and both immunofluorescence and flow cytometry evaluations. The renal transplant is performed according to standard surgical techniques, preferably using an iliac fossa, extraperitoneal approach and utilizing a ureteropyelostomy with the recipient ureter if surgically feasible.

Administration of an Agent that Blocks Costimulation

The recipient can be administered an agent which blocks a costimulatory pathway, e.g., one or both of an agent which inhibits the CD40 ligand-CD40 interaction and an agent which inhibits the CD28-B7 interaction. Such agents can include monoclonal antibodies directed against one of the ligands, or a soluble form of one of the ligands, e.g., anti-CD40 or anti-CD40 ligand antibody, or CTLA4-1gG.

Administration of an Immunosupressant, e.g., Cyclosporine, and Use of Corticosteroids This step is optional An immunosupressant, e.g., cyclosporine, is administered essentially as described in Example 1.

Discontinuation of the Immunosupressant

Discontinuation criteria are similar to those discussed in Example 1.

Clinical laboratory tests, baseline immunologic assessment of the recipient, evaluation of the transplant donor are performed essentially as is described in Example 1.

Other Embodiments

The methods described herein for inducing tolerance to, or promoting the acceptance of, an allogeneic antigen or allogeneic graft can be used where, as between the donor and recipient, there is any degree of mismatch at MHC loci or other loci which influence graft rejection. Preferably, there is a mismatch at at least one MHC locus or at at least one other locus that mediates recognition and rejection, e.g., a minor antigen locus. With respect to class I and class II MHC loci, the donor and recipient can be: matched at class I and mismatched at class II; mismatched at class I and matched at class II; mismatched at class I and mismatched at class II; matched at class I, matched at class II. In any of these combinations other loci which control recognition and rejection, e.g., minor antigen loci, can be matched or mismatched. As stated above, it is preferable that there is mismatch at least one locus. Mismatched at MHC class I means mismatched for one or more MHC class I loci, e.g., in the case of humans, mismatched at one or more of HLA-A, HLA-B, or HLA-C. Mismatched at MHC class II means mismatched at one or more MHC class II loci, e.g., in the case of humans, mismatched at one or more of a DP α, a DPβ, a DQ α, a DQ β, a DR α, or a DR.

The methods described herein for inducing tolerance to an allogeneic antigen or allogeneic graft can be used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests can be used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

The methods of the invention are particularly useful for replacing a tissue or organ afflicted with a neoplastic disorder, particularly a disorder which is resistant to normal modes of therapy, e.g., chemotherapy or radiation therapy. The methods of the invention are also particularly useful in replacing tissue or organ with a patient who is believed to be, based on past experience or current expectations, unreliable with respect to the careful self-administration of chronic immunosuppressive regimens which would otherwise be required following the transplantation of a mismatched mammalian organ or tissue. Methods of the invention can be used for inducing tolerance to a graft, e.g., an allograft, e.g., an allograft from a donor which is mismatched at one or more class I loci, at one or more class II loci, or at one or more loci at each of class I and class II. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

In any of the methods described herein, particularly primate or clinical methods, it is preferable to form mixed chimerism as opposed to entirely replacing the recipient's stem cells with donor cells.

Blockers of the CD40 ligand-CD40 or CD28-B7 interactions (or both) can be administered repeatedly. E.g., blockers can be administered one, two, three, or more times prior to donor bone marrow transplantation. Typically, a pre-bone marrow transplantation dose will be given to the patient about 5 days prior to bone marrow transplantation. Additional, earlier doses 6, 7, or 8 days prior to bone marrow transplantation can also be given. It may be desirable to administer a first treatment, then to repeat pre-bone marrow administrations every 1-5 days. A blocker can also be administered one, two, three, or more times after donor bone marrow transplantation. Typically, a post-bone marrow transplant treatment will be given about 2-14 days after bone marrow transplantation. The post-bone marrow administration can be repeated as many times as needed. If more than one administration is given the administrations can be spaced about 1 week apart. Additional doses can be given if the patient appears to undergo early or unwanted T cell recovery. Preferably, a blocker is administered at least once (and preferably two, three, or more times) prior to donor bone marrow transplantation and at least once (and preferably two, three, or more times) after donor bone marrow transplantation.

While not wishing to be bound by theory the inventor believes that repeated stem cell administration may promote chimerism and possibly long-term deletional tolerance in graft recipients. Accordingly, any method referred to herein which includes the administration of hematopoietic stem cells can further include multiple administrations of stem cells. In preferred embodiments: a first and a second administration of stem cells are provided prior to the implantation of a graft; a first administration of stem cells is provided prior to the implantation of a graft and a second administration of stem cells is provided at the time of implantation of the graft. In other preferred embodiments: a first administration of stem cells is provided prior to or at the time of implantation of a graft and a second administration of stem cells is provided subsequent to the implantation of a graft. The period between administrations of hematopoietic stem cells can be varied. In preferred embodiments a subsequent administration of hematopoietic stem cell is provided: at least two days, one week, one month, or six months after the previous administration of stem cells; at least two days, one week, one month, or six months after the implantation of the graft.

The method can further include the step of administering a second or subsequent dose of hematopoietic stem cells: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells; or generally, as is needed to maintain tolerance or otherwise prolong the acceptance of a graft. Thus, method of the invention can be modified to include a further step of determining if a subject which has received a one or more administrations of hematopoietic stem cells is in need of a subsequent administration of hematopoietic stem cells, and if so, administering a subsequent dose of hematopoietic stem cells to the recipient.

Other embodiments are within the following claims.

What is claimed is:

1. A method of administering to a human recipient a graft from a human, the method comprising:
   administering to the recipient an amount of chemotherapy sufficient to allow the induction of mixed chimerism in the recipient, wherein the chemotherapy comprises administering to the recipient a chemotherapeutic agent which is an antineoplastic agent, an antimetabolite, or a radiomimetic agent;
   administering to the recipient, an amount of thymic irradiation sufficient to kill or otherwise inactivate recipient thymocytes;
   administering to the recipient, an antibody that depletes T cells;
   administering to the recipient, donor hematopoietic progenitor cells, wherein the hematopoietic progenitor cells are enriched for $CD34^+$ cells prior to the administering; implanting the graft into the recipient, wherein the graft is an organ graft selected from a heart, pancreas, liver, or kidney graft; and
   administering to the recipient, a non-chronic course of an immunosuppressant.

2. The method of claim 1, wherein the amount of thymic irradiation is 700 cGy.

3. The method of claim 1, wherein the method further includes, prior to one or more administration of an antibody that depletes T cells, administering to the recipient a steroid.

4. The method of claim 1, wherein the non-chronic course is a 35-day course of cyclosporine followed by 7 days of tapering and ending on day 42.

5. The method of claim 1, further comprising performing a splenectomy on the recipient.

6. The method of claim 1, wherein the antibody that depletes T cells is an anti-CD2 monoclonal antibody.

7. The method of claim 1, further comprising administering to the recipient an anti-B cell antibody.

8. A method of administering to a human recipient a graft from a human, the method comprising:
   administering to the recipient an amount of chemotherapy sufficient to allow the induction of mixed chimerism in the recipient, wherein the chemotherapy comprises administering to the recipient a chemotherapeutic agent which is an antineoplastic agent, an antimetabolite, or a radiomimetic agent;

administering to the recipient, an amount of thymic irradiation sufficient to kill or otherwise inactivate recipient thymocytes;

administering to the recipient, an antibody that depletes T cells, wherein the antibody that depletes T cells is an anti-CD2 monoclonal antibody;

administering to the recipient, donor hematopoietic progenitor cells, wherein the hematopoietic progenitor cells are enriched for $CD34^+$ cells prior to the administering; implanting the graft into the recipient, wherein the graft is an organ graft selected from a heart, pancreas, liver, or kidney graft;

administering to the recipient an anti-B cell antibody; and administering to the recipient, a non-chronic course of an immunosuppressant.

9. The method of claim 8, wherein the amount of thymic irradiation is 700 cGy.

10. The method of claim 8, wherein the anti-CD2 monoclonal antibody is administered on days −4, −3, −2, −1.

11. The method of claim 8, wherein the method further includes, prior to one or more administration of an antibody that depletes T cells, administering to the recipient a steroid.

12. The method of claim 8, wherein the non-chronic course is a 35-day course of cyclosporine followed by 7 days of tapering and ending on day 42.

13. The method of claim 8, further comprising performing a splenectomy on the recipient.

14. A method of administering to a human recipient a graft from a human, the method comprising:

administering to the recipient an amount of chemotherapy sufficient to allow the induction of mixed chimerism in the recipient, wherein the chemotherapy comprises administering to the recipient a chemotherapeutic agent which is cyclophosphamide;

administering to the recipient, an amount of thymic irradiation sufficient to kill or otherwise inactivate recipient thymocytes;

administering to the recipient, an antibody that depletes T cells;

administering to the recipient, donor hematopoietic progenitor cells;

implanting the graft into the recipient, wherein the graft is an organ graft;

administering to the recipient an anti-B cell antibody; and administering to the recipient, a non-chronic course of an immunosuppressant.

15. The method of claim 14, wherein the amount of thymic irradiation is 700 cGy.

16. The method of claim 14, wherein the antibody that depletes T cells is an anti-CD2 monoclonal antibody.

17. The method of claim 16, wherein the anti-CD2 monoclonal antibody is administered on days −4, −3, −2, −1.

18. The method of claim 14, wherein the method further includes, prior to one or more administration of an antibody that depletes T cells, administering to the recipient a steroid.

19. The method of claim 14, wherein the non-chronic course is a 35-day course of cyclosporine followed by 7 days of tapering and ending on day 42.

20. The method of claim 14, further comprising performing a splenectomy on the recipient.

* * * * *